(12) United States Patent
Mailaender et al.

(10) Patent No.: US 9,743,907 B2
(45) Date of Patent: Aug. 29, 2017

(54) TOOL FOR OPENING AND CLOSING A TRANSDUCER HOUSING

(71) Applicants: KONINKLIJKE PHILIPS N.V., Eindhoven (NL); PHILIPS DEUTSCHLAND GMBH, Hamburg (DE)

(72) Inventors: Siegfried Mailaender, Dusslingen (DE); Oliver Schmitz, Monschau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 327 days.

(21) Appl. No.: 14/432,495

(22) PCT Filed: Sep. 25, 2013

(86) PCT No.: PCT/IB2013/058855
§ 371 (c)(1),
(2) Date: Mar. 31, 2015

(87) PCT Pub. No.: WO2014/053958
PCT Pub. Date: Apr. 10, 2014

(65) Prior Publication Data
US 2015/0216501 A1 Aug. 6, 2015

Related U.S. Application Data

(60) Provisional application No. 61/708,716, filed on Oct. 2, 2012.

(51) Int. Cl.
*A61B 8/08* (2006.01)
*A61B 8/00* (2006.01)

(52) U.S. Cl.
CPC .......... *A61B 8/0866* (2013.01); *A61B 8/4411* (2013.01); *A61B 8/4444* (2013.01); *A61B 8/4455* (2013.01)

(58) Field of Classification Search
CPC ... A61B 8/0866; A61B 8/4411; A61B 8/4444; A61B 8/4455; B25B 23/0085; B25B 13/48; B67B 7/18
See application file for complete search history.

(56) References Cited

U.S. PATENT DOCUMENTS 3,625,093 A 12/1971 Freiburghaus
3,930,427 A 1/1976 Addor
(Continued)

FOREIGN PATENT DOCUMENTS

EP 0749722 A2 12/1996

*Primary Examiner* — David B Thomas (57) ABSTRACT

The present invention relates to transducer housing and a tool for opening and closing the transducer housing (20). The transducer housing comprises a base body (22) and a lid (24) which are releasable coupled with a rotational coupling (26). The lid (24) comprises a contact area (42) formed to be engaged by a driving pin (64) of the tool (10) in order to open or close the transducer housing (20) upon a rotation of the lid (24) relative to the base body (22). The tool (10) comprises a base portion (12) and an upper portion (14) that are coupleable wherein the upper portion can be rotated relative to the base portion. When coupled the upper portion and base portion may enclose the transducer housing such that upon a rotational movement of the upper portion (14) relative to the base portion (12) the driving pin (64) of the upper portion (14) engages with the contact area (42) of the lid (24) causing the lid (24) of the transducer housing (20) to move relative to the base body (22) of the transducer housing (20) resulting in an opening or closing of the transducer housing.

15 Claims, 8 Drawing Sheets

(56) References Cited

U.S. PATENT DOCUMENTS

| | | |
|---|---|---|
| 4,958,518 A | 9/1990 | Duenstl et al. |
| 5,770,153 A | 6/1998 | Wagner |
| 5,882,300 A | 3/1999 | Malinouskas et al. |
| 7,510,096 B2 | 3/2009 | Wang |
| 8,038,025 B2 | 10/2011 | Stark et al. |
| 2003/0036702 A1 | 2/2003 | Davidsen |
| 2009/0223853 A1 | 9/2009 | Kim |
| 2013/0120992 A1* | 5/2013 | Deurenberg ............ F21V 15/01 362/249.01 |

* cited by examiner

TOOL FOR OPENING AND CLOSING A TRANSDUCER HOUSING

CROSS REFERENCE TO RELATED APPLICATIONS

This application is a national filing of PCT application Serial No. PCT/IB2013/058855, filed Sep. 25, 2013, published as WO 2014/053958 A1 on Apr. 10, 2014, which claims the benefit of U.S. provisional application Ser. No. 61/708,716 filed Oct. 2, 2012, which is incorporated herein by reference.

FIELD OF THE INVENTION

The present invention relates to a tool for opening and closing a transducer housing, in particular a housing of a fetal monitoring transducer. Further, the present invention relates to a kit comprising such a tool and such a transducer housing.

BACKGROUND OF THE INVENTION

In the past decades a lot of research has been directed to fetal monitoring transducers and devices. These devices are used to either record the fetal heart beat and the uterine contractions during pregnancy and birth or to create images of the fetus in the womb. For the latter one obstetric ultrasonography is usually performed, wherein sonography is used to visualize the embryo or fetus in its mother's uterus (womb). This procedure is a standard part of prenatal care, as it provides a variety of information regarding the health of the mother and the fetus, the progress of the pregnancy, and further information on the baby before and during birth.

In order to record the uterine contractions during pregnancy and birth slightly different machines are used. The machines used to perform such monitoring are called cardiotocographs, more commonly known as electronic fetal monitors (EFM).

In both above-mentioned fetal monitoring devices one or more ultrasonic transducers or other ultrasonic-based sensors are used. These ultrasonic transducers and other electronic periphery devices need to be encapsulated in a liquid-tight housing. Usually two half-shells are used to provide an encapsulated volume for the measurement transducers and the peripheral devices of the fetal monitoring apparatus.

One issue that commonly appears is the serviceability of the transducers and the peripheral devices. After usage the transducer housings have to be cleaned and disinfected. On the other hand, the transducer housing needs to be absolutely liquid-tight, as the housing is usually contaminated with a lot of blood and mucus if used during birth. In most cases the two half-shells of the transducer housing are therefore either glued together or joined with each other using screws.

In case the two half-shells of the transducer housing are glued together this has a main (negative) impact on the serviceability of the transducer housing. In case the two housing parts are glued together, it is hard to open the transducer housing in order to repair or replace any part inside the housing, since the glue bond in this case needs to be released. Releasing the glue bond might be difficult and could also destroy parts of the housing.

A connection of the two half-shells of the transducer housing via screws is also not advantageous. First of all, screws have a negative visual impact on the transducer housing and could negatively influence the design of the transducer housing. Further, the metal parts of the screws could have a negative influence to a radio system of a wireless transducer. Even further, the screws occupy space within the transducer housing. Apart from that gaps and sharp edges might occur when using screws as connection parts, which could lead to unwanted injuries of the patient. Another negative effect is that a physician him/herself could try to open the transducer housing in order to repair or clean the ultrasonic transducer or peripheral devices connected thereto. However, such a self-repair shall be prevented in any case.

There are strong regulations in the medical field that stipulate that a medical device may not be opened by any unauthorized person, but only by authorized persons that are in possession of a special opening tool.

SUMMARY OF THE INVENTION

Therefore, it is an object of the present invention to provide an easy to disinfect and easy to use screwless connection system for a fetal monitoring transducer housing. Furthermore, it is an object to provide a tool for opening and closing a transducer housing of a fetal monitoring device that serves as the only tool system that may be used to open and close the transducer housing. The usage of the tool shall be intuitive and shall not require a too high expenditure of energy.

In a first aspect of the present invention, a tool for opening and closing a transducer housing having two housing parts, a base body and a lid, is provided, the two housing parts being coupleable with each other via a rotational coupling, wherein the tool comprises:
  a base portion forming a bowl for receiving the transducer housing and preventing a rotation of the base body of the transducer housing relative to the base portion of the tool around an axial direction of the tool; and
  an upper portion that is coupleable with the base portion, wherein a movement of the upper portion relative to the base portion in a radial direction, which is perpendicular to the axial direction, is mechanically prevented when the upper portion and the base portion are coupled with each other;
  wherein the base portion comprises a first engagement member and wherein the upper portion comprises a second engagement member which engages with the first engagement member when the upper portion and the base portion are coupled with each other,
  wherein the upper portion further comprises a driving pin having a driving area for contacting a corresponding contact area of the lid of the transducer housing for causing the lid of the transducer housing to move relative to the base body of the transducer housing in order to open or close the rotational coupling upon a rotational movement of the upper portion relative to the base portion around the axial direction; and
  wherein an engagement of the second engagement member with the first engagement member prevents a movement of the upper portion relative to the base portion along the axial direction during a contact between the driving area of the driving pin and the contact area of the lid of the transducer housing.

In a further aspect of the present invention a kit is presented that comprises:
  a tool according to any of claims 1 to 14, and
  a transducer housing having two housing parts, a base body and a lid, that are coupleable with each other via a rotational coupling to form a liquid-tight housing, wherein the lid comprises a contact area that is adapted to be contacted by a driving pin of the tool to open or close the transducer housing.

In a still further aspect of the present invention a transducer housing is presented that comprises:
- a base body, and
- a lid,
- wherein the base body and the lid are coupleable with each other via a rotational coupling,
- wherein the lid comprises a contact area that is adapted to be contacted by a driving pin of a tool in order to open or close the transducer housing upon a rotation of the lid relative to the base body around an axial direction, and
- wherein the base body has a shape that is adapted to a base portion of said tool for preventing a rotation of the base body relative to the base portion of the tool around the axial direction.

Preferred embodiments of the invention are defined in the dependent claims. It shall be understood that the claimed kit and the claimed transducer housing has similar and/or identical preferred embodiments as the claimed tool and as defined in the dependent claims.

One of the central points of the present invention is the provision of a transducer housing with two housing parts, that are herein denoted as the base body and the lid, which may be coupled with each other via a rotational coupling. The rotational coupling is preferably integrated into the transducer housing. A rotational coupling shall be any coupling that allows coupling the lid and the base body with each other upon a rotation of the two parts relative to each other. Well-known examples are a threaded coupling or a bayonet mount. However, also other rotational couplings may be used without leaving the scope of the present invention.

According to a preferred embodiment the rotational coupling is realized as a bayonet mount. The integrated bayonet mount provides locking and release of the two half-shells (two housing parts) of the transducer housing. Instead of integrating a lever or any other element into the lid of the transducer housing that allows to lock and/or release the bayonet mount of the transducer housing, the transducer housing is designed such that it may be only opened and/or closed using the herein presented opening and closing tool. An unintentional opening or an opening of the transducer housing by an unauthorized person is therefore permitted. Only persons, who are in possession of the herein presented special tool, are able to open the transducer housing. In a hospital, for example, only people working in a service and repair ward may have the herein presented special opening and closing tool, so that only these people are enabled to open and close the transducer housing for service and repair reasons (but not the physician him-herself).

A further advantage of the herein presented transducer housing is an easy cleanability, since it preferable does not have any sharp edges. Most parts of the outer surface of the transducer housing are rounded or concave surfaces. Therefore, a risk of injury is minimized. Since there are no sharp edges, it is very difficult or almost impossible to open the transducer housing without the herein presented tool. An opening simply by hand is not possible, since there are no edges that can be caught in order to exert a sufficiently large torque on the lid of the housing for opening the bayonet mount.

It is to be noted that the term "transducer housing" shall denote any type of housing that is suitable for encasing a transducer. It is not restricted to any specific type, shape or size. It does not have to include the transducer itself.

In order to open and/or close the transducer housing, the lid of the transducer housing comprises a contact area that may be contacted by the above-mentioned driving pin of the tool. A form fit between the tool and the transducer housing is preferably established that allows to open and/or close the lid of the transducer housing. Since the transducer housing makes use of a bayonet mechanism that is integrated into the two housing parts (the base body and the lid), there is no visual impact to the transducer shell. Since no screws have to be used, the bayonet mount also eliminates the negative influence of the metal parts that could disturb the radio system of a wireless transducer. The absence of gaps and interrupted surfaces also makes it easy to clean the transducer device. The avoidance of glued shells (as used in many prior art devices) allows a non-destructive and easy serviceability of the internal devices that are encapsulated within the transducer housing. The technical features of the herein presented special tool for opening and closing the transducer housing shall be further detailed in the following.

The tool preferably comprises two separate parts, a base portion and an upper portion. The base portion forms a kind of bowl for receiving the transducer housing. If the transducer housing is inserted into said base portion of the tool, a rotation of the base body of the transducer housing relative to the base portion of the tool around the axial direction of the tool is prevented. This rotation prevention may be realized in many ways. In the simplest case a form fit between an inner wall of the base portion of the tool and at least a part of an outer wall of the base body of the transducer housing is realized. The outer wall of the transducer housing may, for example, have the same or corresponding shape as the inner wall of the base portion of the tool in order to create a form fit at the interface between the transducer housing and the tool.

As already stated above the two parts of the tool are preferably realized as two separate parts that are coupleable with each other. The upper portion of the tool serves as a kind of lid that may be attached to the base portion of the tool. Parts of the upper portion may interlock with parts of the base portion to prevent a relative movement in radial direction (perpendicular to the axial direction).

According to an embodiment, the base portion comprises an inner wall and the upper portion comprises an outer wall that faces the inner wall of the base portion when the upper portion and the base portion are coupled with each other. At least a part of said inner wall of the base portion of the tool may form a form fit with at least a part of the outer wall of the upper portion of the tool. This form fit may prevent a movement of the upper portion relative to the base portion in the radial direction.

The engagement between the two parts of the tool may be realized by two or more engagement members: a first engagement member which is arranged on the base portion of the tool and a second engagement member which is arranged on the upper portion of the tool and engages the first engagement member, when the upper portion and the base portion of the tool are coupled with each other. This engagement between the at least two engagement members serves as a mechanical guidance that allows a rotational movement of the upper portion relative to the base portion around the axial direction. A user may thus attach the upper portion to the base portion of the tool and rotate the upper portion by hand around the axial direction relative to the base portion. The user, for example, holds the base portion in one hand while turning the upper portion of the tool relative thereto with the other hand, either clockwise or counter-clockwise, around the axial direction.

A further important part of the tool is the driving pin that is arranged on the upper portion of the tool. When rotating the upper portion of the tool around the axial direction, this driving pin is rotated as well. It comprises a driving area for contacting a corresponding contact area of the lid of the transducer housing. In this way the driving pin exerts a force on the lid of the transducer housing when the upper portion of the tool is rotated around the axial direction relative to the base portion of the tool. This force causes the lid of the transducer housing to rotate synchronically with the upper portion of the tool as soon as a user rotates the upper portion relative to the base portion. The upper portion of the tool therefore acts as a kind of mechanical lever that enables to push the lid of the transducer housing.

During the above-described rotational movement of the upper portion of the tool around the axial direction (caused by a hand movement of the user) the driving pin contacts the lid of the transducer housing and causes it to move relative to the base body of the transducer housing in order to open or close the bayonet mount. Since a form fit between the base portion of the tool and the base body of the transducer housing prevents a rotation of the base body of the transducer housing within the tool, only the lid of the transducer housing is forced into rotation (together with the upper portion of the tool). The base body of the transducer housing thereby remains still. A clockwise rotation of the upper portion of the tool could, for example, cause the bayonet mount to open, while a counter-clockwise of the upper portion of the tool could cause the bayonet mount to close.

During this opening and/or closing procedure it must be ensured that the driving pin of the tool does not only slip over the lid of the transducer housing, since the force would otherwise not be correctly transferred from the tool to the lid of the transducer housing in order to open and/or close it. This is solved according to the present invention in that the engagement of the second engagement member with the first engagement member of the tool prevents a movement of the upper portion of the tool along the axial direction while the driving pin contacts the lid of the transducer housing. The driving pin is therefore also in axial direction pressed onto the lid of the transducer housing.

According to a further embodiment, the movement of the base body of the transducer housing relative to the base portion of the tool around the axial direction is prevented as follows: The inner wall of the base portion may have a cylindrically curved surface area, wherein parts of said inner wall deviate from the cylindrical shape and comprise a planar contact surface for contacting a corresponding contact surface of the transducer housing. The interaction between these two contact surfaces of the tool and the base body of the transducer housing then prevents a rotation of the base body of the transducer housing relative to the base portion of the tool around the axial direction. The planar contact surface of the inner wall of the base portion of the tool may thereto be arranged perpendicular to the circumferential direction of the tool. The circumferential direction in this case denotes the direction that is perpendicular to the axial direction as well as perpendicular to the radial direction of the tool.

However, a rotation of the base body of the transducer housing relative to the base portion of the tool may also be prevented in many other technical ways. The outer wall of the base body of the transducer housing as well as the inner wall of the base portion of the tool could, for example, both have a corresponding octagonal shape such that a form fit is established in-between said two walls that prevents the transducer housing from rotationally moving within the tool.

In the following, the engagement between the upper portion and the base portion of the tool shall be detailed. According to an embodiment of the present invention, the second engagement member is realized as a recess in the upper portion of the tool and the first engagement member is realized as a guiding pin which engages with said recess when the upper portion and the base portion of the tool are coupled with each other. Said recess preferably comprises an insertion section and an adjacent locking section, wherein the insertion section is larger than the locking section. The guiding pin may be inserted into the insertion section and maybe guided into the locking section upon a rotational movement of the upper portion relative to the base portion around the axial direction. The insertion section of the recess within the upper portion should be large enough that the guiding pin may be inserted into the recess with enough clearance. By rotating the upper portion of the tool relative to the base portion of the tool, the guiding pin of the base portion is brought into the adjacent locking section. This locking section should be, in contrast to the insertion section, small enough that there is no clearance anymore between the guiding pin and the locking section of the recess. In this way, the guiding pin may be clamped within the locking section of the recess, so that a movement of the upper portion relative to the base portion of the tool is thereby mechanically prevented in axial direction.

The arrangement of the locking section of the recess within the upper portion of the tool relative to the driving pin is chosen such that the guiding pin of the base portion reaches the locking section before the driving area of the driving pin contacts the contact area of the lid of the transducer housing during a rotational movement of the upper portion. This assures that the upper portion of the tool is first clamped within the base portion of the tool before the driving pin contacts the lid of the transducer housing and exerts a force thereon to open and/or close the transducer housing. The engagement between the guiding pin and the recess (in the locking section) therefore assures that the driving pin does not slip over the lid of the transducer housing without pushing it in circumferential direction.

According to a further embodiment of the present invention, the base portion comprises a third engagement member and the upper portion comprises a fourth engagement member which engages with the third engagement member when the upper portion and the base portion are coupled with each other. Similar as the first engagement member the third engagement member may be realized as a kind of guiding pin and the fourth engagement member may be realized as a recess in the upper portion of the tool (similar to the above-mentioned second engagement member).

Preferably, the third engagement member is designed to be smaller than the first engagement member and the fourth engagement member is designed to be smaller than the second engagement member. In this way the first engagement member (first guiding pin) can only engage with the second engagement member (first recess) and the third engagement member (second guiding pin) can only engage with the fourth engagement member (second recess). In other words, by providing two differently sized guiding pins arranged on the base portion of the tool and two differently sized recesses within the upper portion of the tool, the two parts of the tool may be coupled in only one position. This realizes a kind of poka-yoke. An incorrect coupling of the upper portion and the base portion of the tool is prevented.

According to an even further embodiment, the driving area of the driving pin has a concave shape. The contact area of the lid of the transducer housing has thereto a corresponding convex shape. Such a convex or rounded shape of the contact area of the transducer's lid ensures that the lid may only be opened using the herein presented special tool. A convex or rounded contact area does not offer a large enough target surface in order to open and/or close the transducer's lid by hand or using a conventional tool. Only a correspondingly concave shaped driving pin as provided by the herein presented tool may be used to open and/or close the lid.

According to a further preferred embodiment, the upper portion of the tool does not only comprise one driving pin, but comprises two driving pins: a first driving pin with a first driving area for opening the bayonet mount of the transducer housing upon a rotational movement of the upper portion relative to the base portion around the axial direction, and a second driving pin with a second driving area for closing the bayonet mount of the transducer housing upon an oppositely oriented rotational movement. The first driving pin and the second driving pin are preferably arranged on opposite sides of the tool's upper portion. The first driving area of the first driving pin preferably faces in an opposite direction as the second driving area of the second driving pin. If the user wants to close the lid of the transducer housing instead of opening it, he/she just has to flip the tool's upper portion by 180° and use it upside-down. It is to be noted that this is only a mandatory feature. The second driving pin may, in a variant, also be arranged on the same side of the tool's upper portion as the first driving pin.

BRIEF DESCRIPTION OF THE DRAWINGS

These and other aspects of the invention will be apparent from and elucidated with reference to the embodiment(s) described hereinafter. In the following drawings FIG. 5 shows an embodiment of a tool according to the present invention, in a perspective view (FIG. 5A) and in a top view (FIG. 5B), FIG. 6 shows the tool according to the present invention in a second position, in a perspective view (FIG. 6A) and in a top view (FIG. 6B), FIG. 7 shows the tool according to the present invention in a third position, in a perspective view (FIG. 7A) and in a top view (FIG. 7B)

DETAILED DESCRIPTION OF THE DRAWINGS

Figure 1:
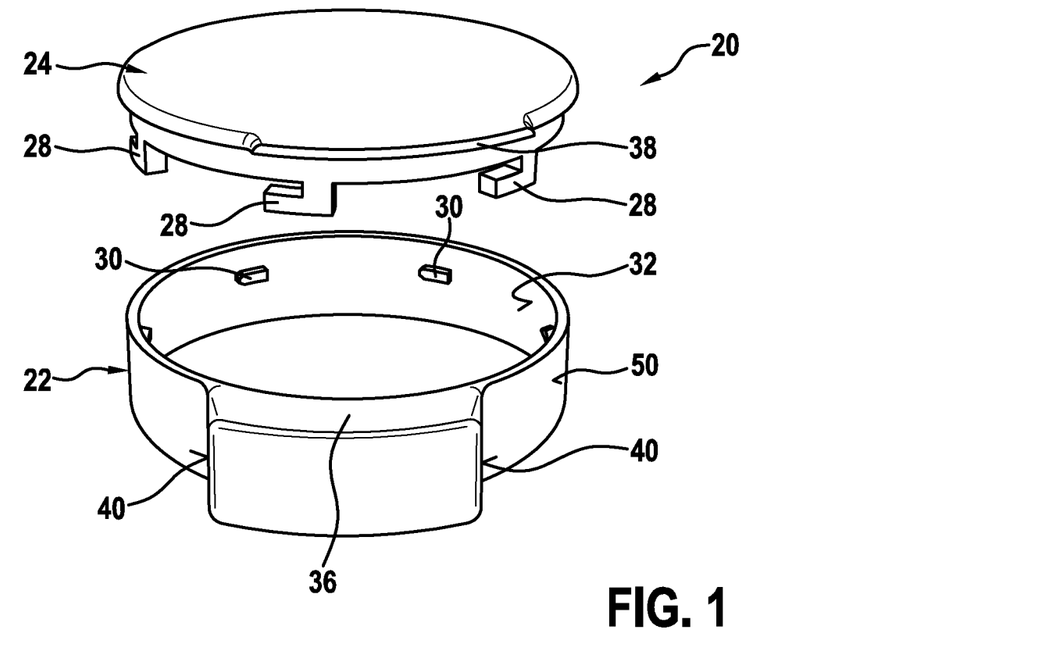
FIG. 1 shows an exploded view of a transducer housing according to an embodiment of the present invention.
Figure 2:
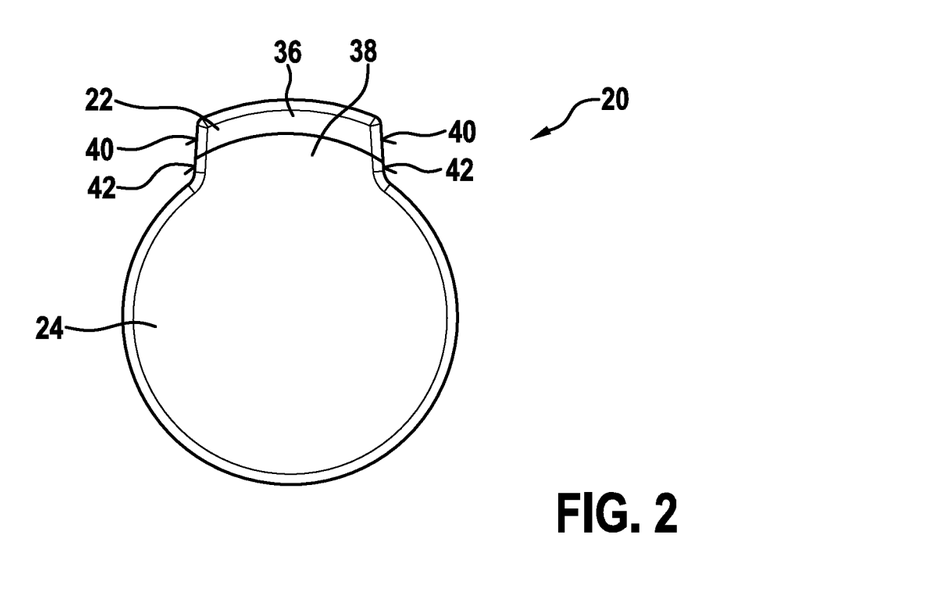
FIG. 2 shows a top view of the transducer housing shown in FIG. 1, FIG. 3 schematically illustrates different positions of a bayonet mount that is arranged within the transducer housing shown in FIG. 1.

FIGS. 1 and 2 illustrate the principle design of a transducer housing 20 which may be opened and closed with the tool 10 according to the present invention. The tool 10 will be described further below with reference to FIGS. 5 to 9. For a better understanding of the reader the principle design of the transducer housing 20 that may be opened and closed with the tool 10 shall be explained first.

As illustrated in FIG. 1 the transducer housing 20 comprises two housing parts, a base body 22 and a lid 24. The base body 22 and the lid 24 form two half-shells of the transducer housing 20 to provide an encapsulated volume inside the transducer housing 20. In practice, several transducers, sensors and peripheral electronic devices of an obstetric ultrasonography device or an electronic fetal monitor (EFM) are arranged in this encapsulated volume.

Figure 3A:
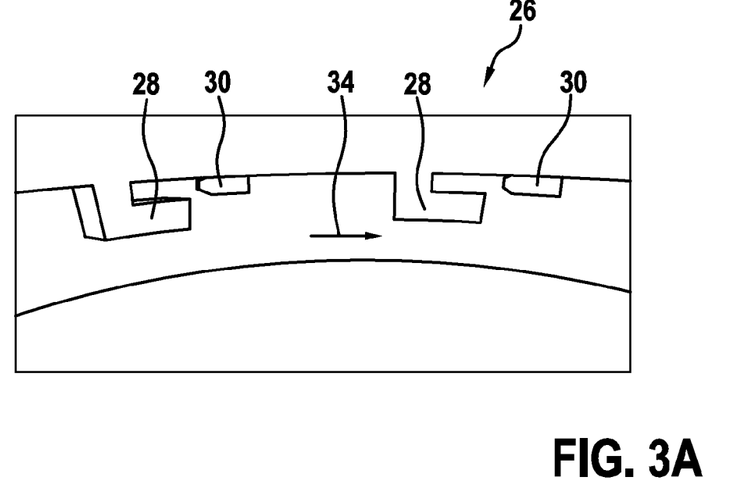
Figure 3B:
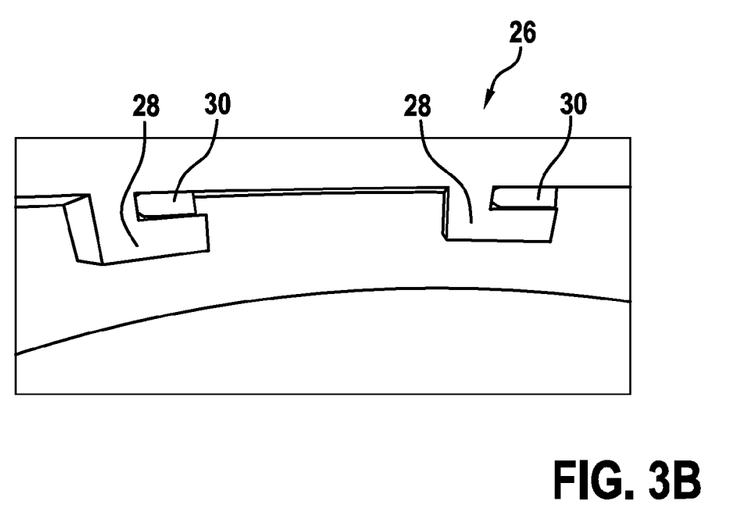

A rotational coupling 26, which is in detail illustrated in FIGS. 3A and 3B, is used as a connection means to connect the lid 24 with the base body 22. This rotational coupling is, according to the herein presented embodiment, realized as a bayonet mount 26. This bayonet mount 26 comprises several undercuts 28 that are arranged on the bottom side of the lid 24 and a plurality of corresponding bayonet noses 30 that are arranged on a circumferential inner wall 32 of the base body 22.

As it is schematically illustrated in FIG. 3A by arrow 34 the lid 24 may be coupled with the base body 22 by a clockwise rotation of the lid 24 relative to the base body 22 of the transducer housing 20. Upon this rotation the undercuts 28 engage with the bayonet noses 30 to form a mechanically secure but releasable connection between the lid 24 and the base body 22. FIG. 3B illustrates the closed position of the bayonet mount 26.

It is to be understood that the bayonet mount 26 may also be inverted compared to the illustrated example. The bayonet noses 30 could also be arranged on the lid 24 and the undercut members 28 could be arranged on the inner wall 32 of the base body 22. Likewise it would also be possible to invert the alignment of the undercut members 28 so that the bayonet mount 26 would be closed upon a counter-clockwise rotational movement of the lid 24 relative to the base body 22, and opened upon a clockwise rotational movement of the lid 24 relative to the base body 22.

According to an embodiment the undercut members 28 and the bayonet noses 30 may be arranged asymmetrically. This means that the distances between the bayonet noses 30 may (slightly) differ. Accordingly, the lid 24 may be attached to the base body 22 in only one correct position. This serves as a poka-yoke feature supporting the user to correctly attach the lid 24 to the base body 22 of the transducer housing 20.

As it is shown in FIG. 1 the base body of the transducer housing preferably has a substantially cylindrical shape. In correspondence thereto the lid 24 has, in a plane view (see FIG. 2), a substantially circular shape. However, parts of the base body 22 and parts of the lid 24 differ from said substantially cylindrical or substantially circular shape, respectively. These parts of the base body 22 and the lid 24 are indicated in FIGS. 1 and 2 by reference numerals 36 and 38.

The part 36 of the base body 22 is realized as a kind of projection of the cylindrical main part of the base body 22. Said projection 36 comprises two planar contact surfaces 40 that may be used as counter supports for contacting corresponding contact surfaces of the tool 10 and preventing a rotational movement of the base body 22 within the tool 10.

Similarly, the projection 38 that is arranged on one side of the lid 24 comprises two contact areas 42 on its lateral sides. These contact areas 42 can be contacted by a driving pin of the tool 10 in order to exert a force onto the lid 24 for rotating the lid 24 relative to the base body 22 of the transducer housing 20 to open or close the bayonet mount 26. The detailed principle how the bayonet mount 26 is opened with the tool 10, will be explained in detail further below with reference to FIGS. 5 to 9.

The described contact areas 42 of the lid 24 preferably have a rounded, convex shape. Even though this is not a mandatory feature such a rounded, convex shape prevents that the lid 24 may be rotated by hand or by using a conventional tool. No means or levers are integrated into the lid 24 that could be used to easily rotate the lid 24 by hand in order to open the bayonet mount 26. The bayonet mount 26 shall furthermore be tight enough so that one cannot exert a sufficient momentum onto the lid 24 by hand. Therefore, the lid 24 can only be opened using the tool 10. This shall be especially ensured due to the strong regulations in the medical field that stipulate that a medical device may not be opened by any unauthorized person.

Figure 4A:
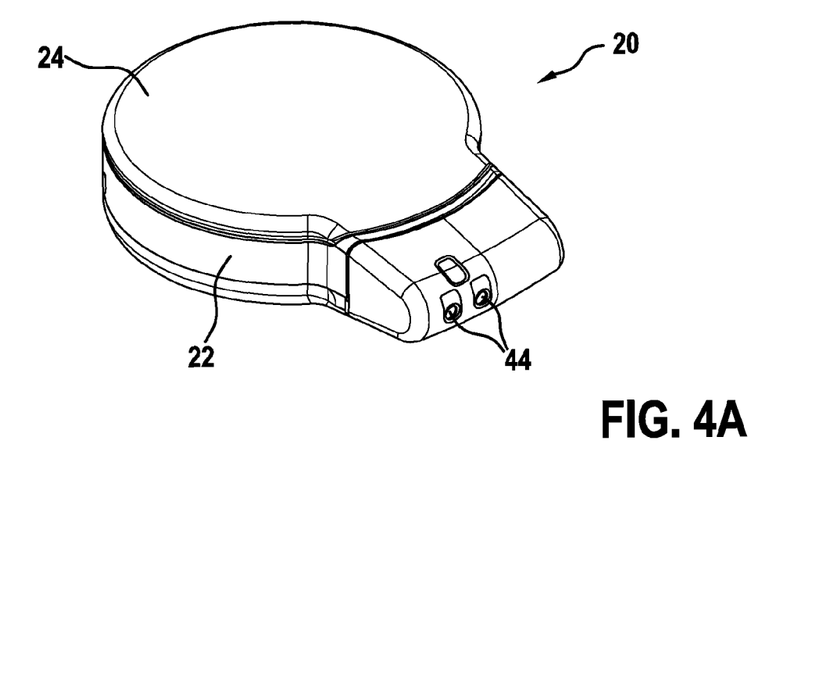
FIG. 4 shows schematic views of the transducer housing in a closed position (FIG. 4a) and in an open position (FIG. 4B)
Figure 4B:
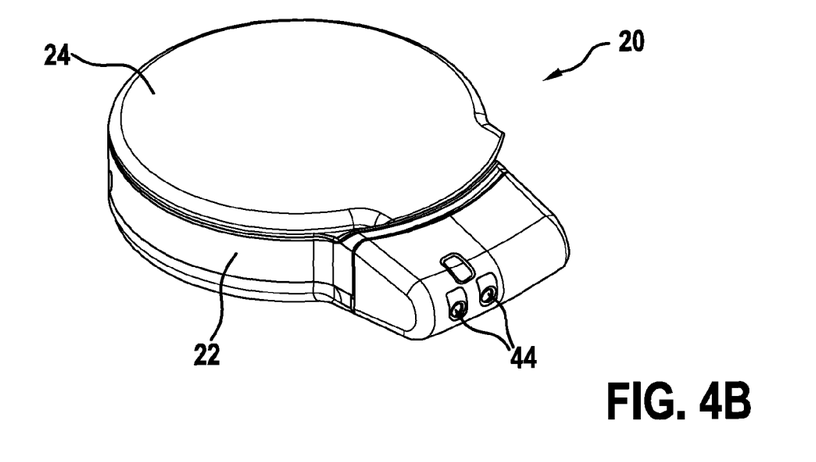

FIG. 4 again shows respective views of the transducer housing 20, wherein FIG. 4A shows the lid 24 in its closed position, and FIG. 4B shows the lid 24 in its open position. It is clear that the position of the bayonet mount 26 illustrated in FIG. 3B corresponds to the closed position of the lid 24 (illustrated in FIG. 4A) and the open position of the bayonet mount 26 illustrated in FIG. 3A corresponds to the open position of the lid 24 (illustrated in FIG. 4B). From FIG. 4 it may be further seen that the transducer housing 20 may comprise several connectors 44. These connectors 44 can have different technical functions. For example, a power supply may be connected to the transducer. On the other hand, these connectors could serve as a connection to a base station in order to transmit the gained ultrasonic transducer signals. It shall be noted that the transducers inside the transducer housing 20 may be connected to such a base station either via a wireless connection or via a hard-wired connection.

Figure 5A:
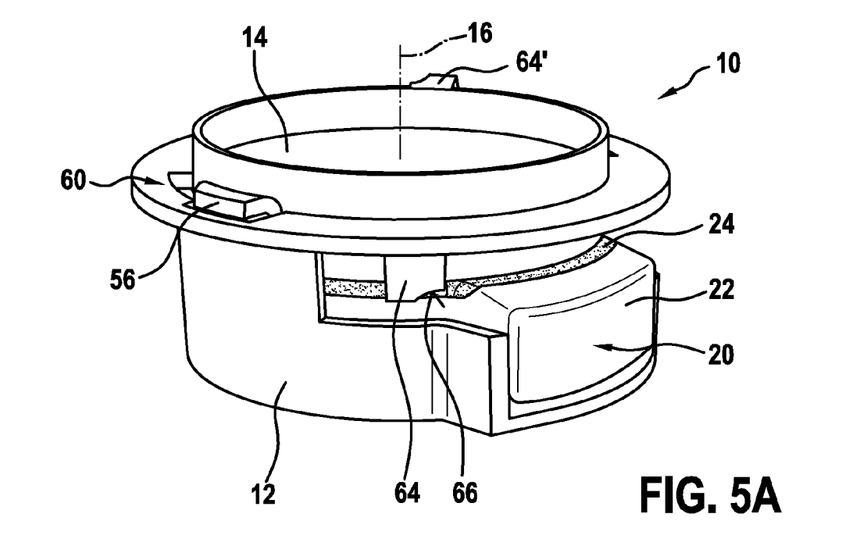

In the following the details of the tool 10 according to the present invention will be presented. As illustrated in FIG. 5A the tool 10 comprises a base portion 12 and an upper portion 14. The base portion 12 has the form of a bowl that is configured to receive the transducer housing 20. Since the shape of said bowl is adapted to the shape of the base body 22 of the transducer housing 20, the base portion 12 of the tool 10 prevents a rotation of the base body 22 of the transducer housing 20 within the tool 10 around an axial direction 16. This form fit also prevents a relative movement of the base body 22 of the transducer housing 20 within the base portion 12 of the tool 10 along a radial direction 18.

Figure 10:
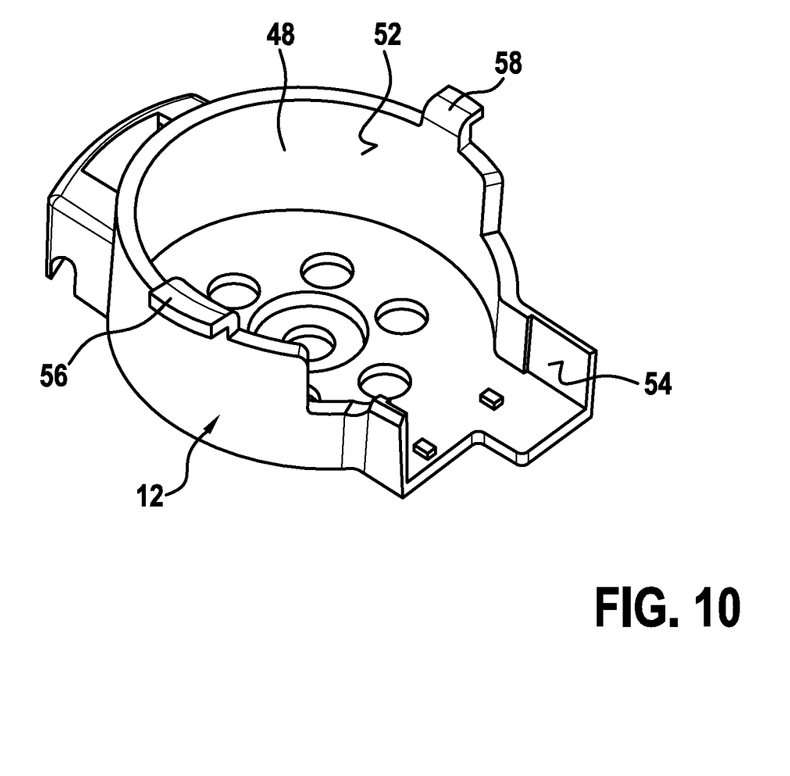
FIG. 10 shows a perspective view of a base portion of the tool.

FIG. 10 shows an enlarged view of the base portion 12 of the tool 10. It can be seen that the base portion 12 comprises an inner wall 48 that is adapted to the outer wall 50 of the base body 22 of the transducer housing 20 (compare to FIG. 1). This inner wall 48 preferably has a cylindrically curved surface area 52. However, parts of said inner wall 48 deviate from the cylindrical shape and comprise a planar contact surface 54 which is adapted to contact the contact surface 40 of the transducer housing 20 for preventing a rotation of the base body 22 of the transducer housing 20 relative to the base portion 12 of the tool 10 around the axial direction 16 (along the circumferential direction 46).

Figure 5B:
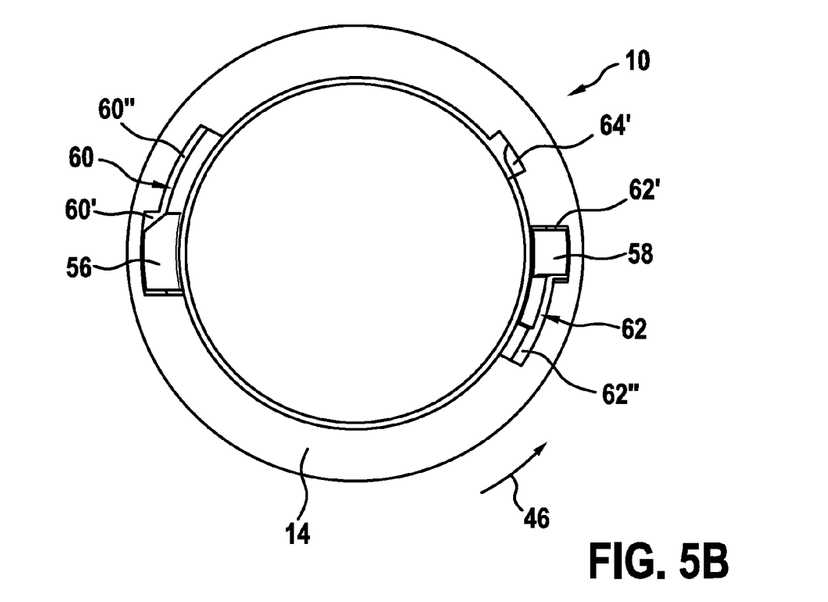

The base portion 12 further comprises to guiding pins, a first guiding pin 56 and a second guiding pin 58 (see e.g. FIG. 5B). The first and the second guiding pins 56, 58 are also denoted as first engagement member 56 and third engagement member 58. It is to be noted that, depending on the size, only one engagement member 56, 58 would also be sufficient. However, it is preferred to provide at least two such engagement members 56, 58.

The two guiding pins 56, 58 are used to couple the tool's base portion 12 with the tool's upper portion 14. The upper portion 14 thereto comprises two recesses, a first recess 60 and a second recess 62 (see e.g. FIG. 5B). These first and second recesses 60, 62 are herein also denoted as second engagement member 60 and fourth engagement member 62.

As illustrated in FIG. 5B the first guiding pin 56 engages with the first recess 60, whereas the second guiding pin 58 engages with the second recess 62. The guiding pins 56, 58 as well as the recesses 60, 62 are differently sized. Even though this is not a mandatory feature it makes it easy for a user to correctly attach the upper portion 14 onto the base portion 12, since an incorrect attachment is prevented. The larger guiding pin 56 (first engagement member) can only engage with the larger recess 60 (second engagement member) and the smaller guiding pin 58 (third engagement member) can only engage with the smaller recess 62 (fourth engagement member).

On the one hand, the engagement between the guiding pins 56, 58 and the recesses 60, 62 serves as a guidance for a rotation of the upper portion 14 relative to the base portion 12 and, on the other hand, prevents a movement of the upper portion 14 to the base portion 12 along the axial direction 16 during opening and/or closing the lid 24 of the transducer housing 20.

In order to open the bayonet mount 26 of the transducer housing 20 the tool's upper portion 14 is simply rotated relative to the tool's base portion 12 around the axial direction 16 (along the circumferential direction 46). Upon this rotational movement a driving pin 64, that is arranged on the tool's upper portion 14, contacts the lid 24 of the transducer housing 20 and causes the lid 24 to rotate as well (synchronously with the rotational movement of the tool's upper portion 14). Since the base body 22 of the transducer housing 20 is fixed within the tool's base portion 12, this rotational movement of the lid 24 opens the bayonet mount 26.

The driving pin 64 is configured to establish a form fit with the contact area 42 of the lid 24. In order to establish this form fit the driving pin 64 preferably comprises a driving area 66 that has a concave shape (corresponding to the convex shape of the contact area 42 of the lid 24; compare to FIG. 2).

Figure 6A:
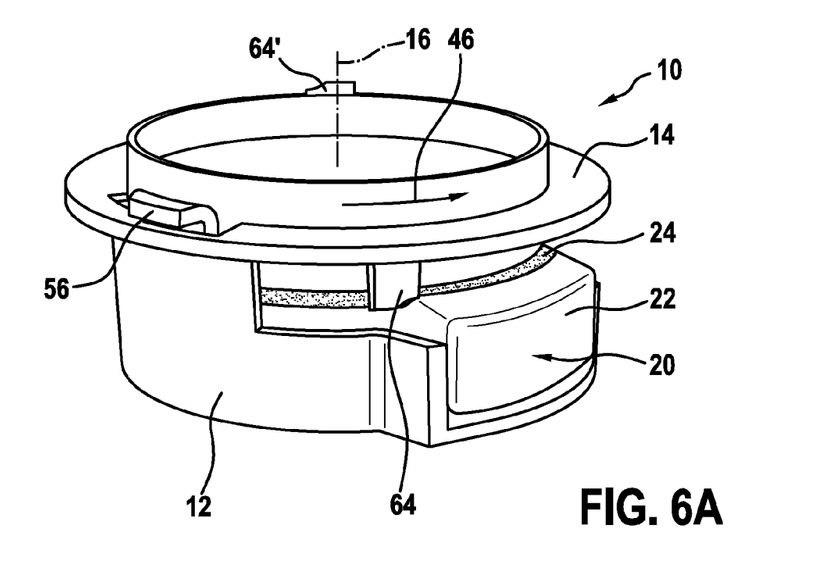
Figure 6B:
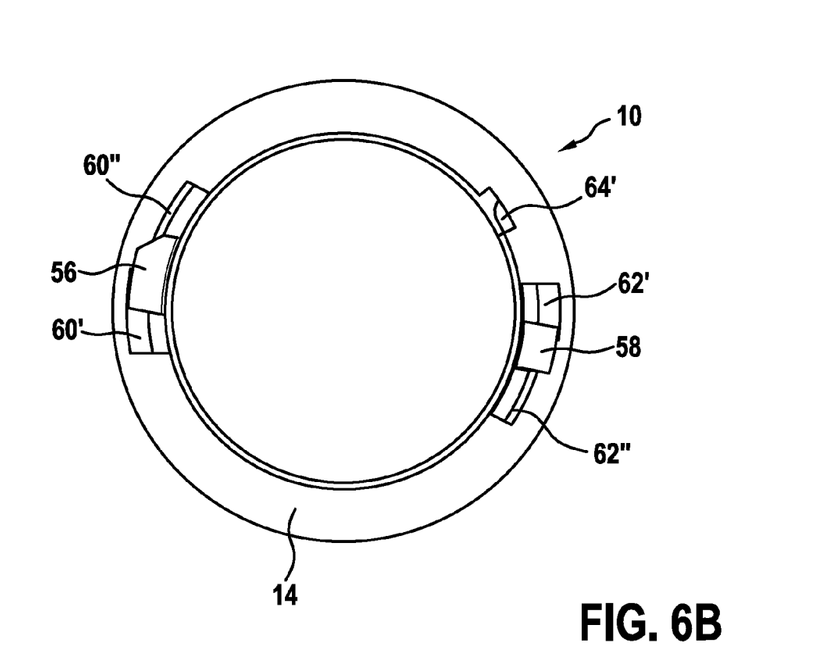
Figure 7A:
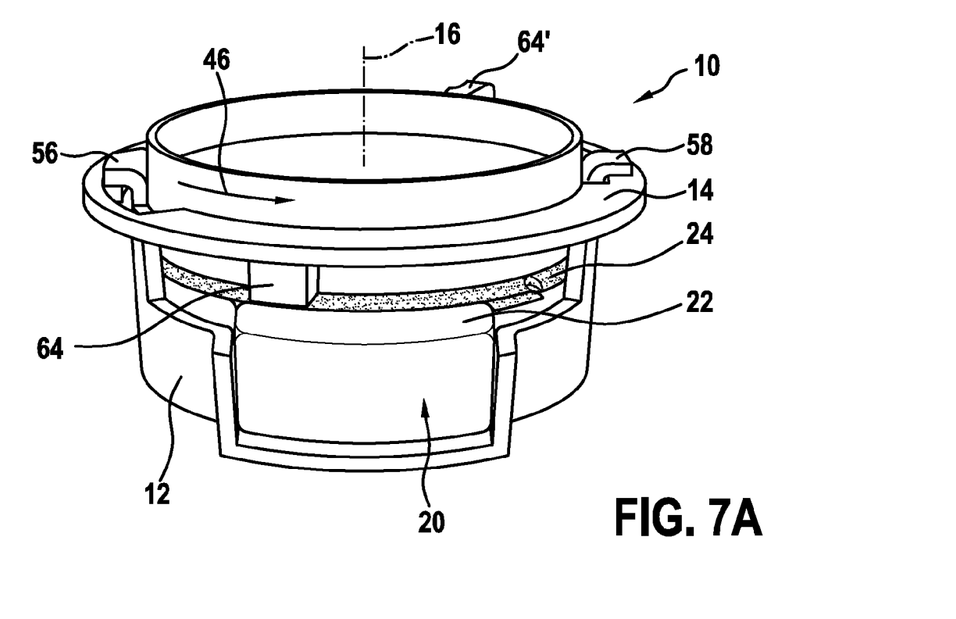
Figure 7B:
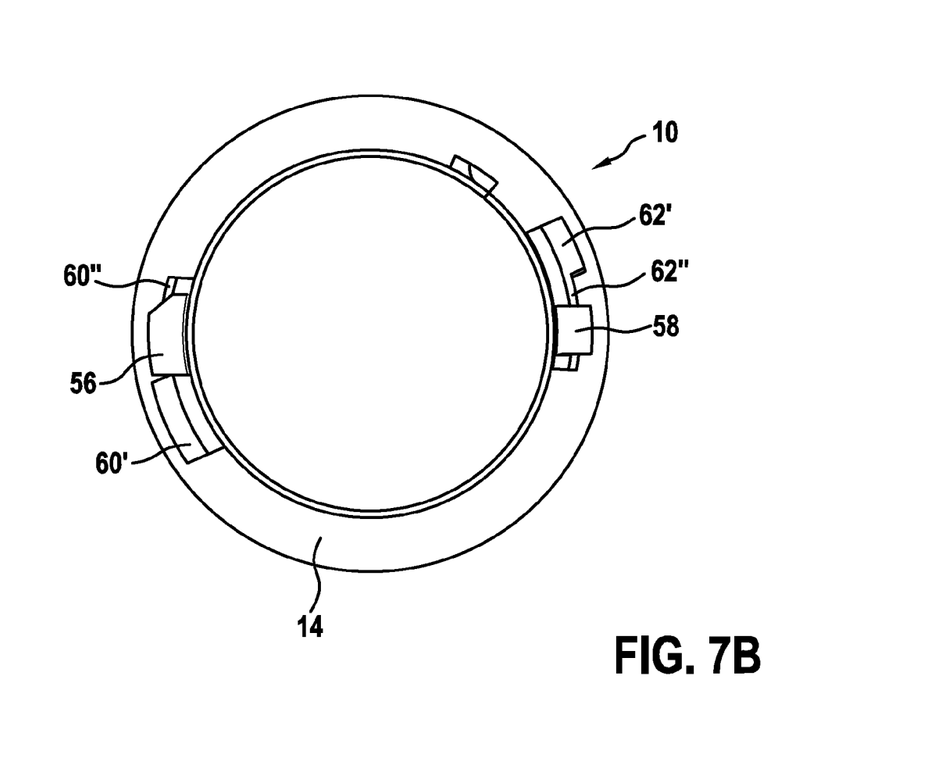

FIGS. 5 to 7 show different snapshots at subsequent points in time for illustrating the technical principle of the tool 10 during opening the lid 24 of the transducer housing 20. FIGS. 5A and 5B show the starting position after the tool's upper portion 14 has been attached to the tool's base portion 12. In this position the driving pin 64 does not contact the lid 24 (see FIG. 5A).

As it can be seen in FIG. 5B the larger guiding pin 56 is in this situation arranged in an insertion section 60' of the recess 60 and the smaller guiding pin 58 is arranged in an insertion section 62' of the recess 62. Both recesses 60, 62 have the form similar to an L and comprise larger insertion sections 60', 62' and smaller (narrower) sections 60", 62", which are herein denoted as locking sections 60", 62". If the guiding pins 56, 58 are arranged within the insertion sections 60', 62' of the recesses 60, 62 the tool's upper portion 14 is still free to move in axial direction 16 relative to the tool's base portion 12. As soon as the guiding pins 56, 58 are led into the locking sections 60", 62" of the recesses 60, 62 (upon a rotation of the upper portion 14 around the axial direction 16), the guiding pins 56, 58 clamp the tool's upper portion 14 and prevent a movement of the upper portion 14 relative to the base portion 12 in axial direction 16. It is to be noted that in this case the tool's axial direction 16 falls together with the axial direction of the transducer housing 20.

In the starting position shown in FIGS. 5A and 5B the driving pin 64 does not contact the lid 24 and the two guiding pins 56, 58 are arranged within the insertion sections 60', 62' (see FIG. 5B). If the tool's upper portion 14 is then rotated counter-clockwise around the axial direction 16, the driving pin 64 will contact the lid 24 (see FIG. 6A), wherein a form fit between the driving area 66 of the driving pin 64 and the contact area 42 of the lid 24 is established. In this situation a relative movement of the tool's upper portion 14 along the axial direction 16 is prevented through the engagement between the guiding pins 56, 58 and the recesses 60, 62 (see FIG. 6B).

As it can be seen in FIG. 6B the guiding pins 56, 58 are then already arranged within the locking sections 60", 62" of the recesses 60, 62. The arrangement of the locking sections 60", 62" relative to the driving pin 64 is chosen such that the guiding pins 56, 58 of the base portion 12 reach the locking sections 60", 62" before the driving area 66 of the driving pin 64 contacts the contact area 42 of the lid 24 during a rotational movement of the tool's upper portion 14 around the axial direction 16. In other words, the upper portion 14 is fixed in axial direction 16 before the driving pin 64 reaches the lid 24 of the transducer housing 20. The driving pin 64 does therefore not only exert a force in circumferential direction 46 onto the lid 24, but is also pressed in axial direction 16 onto the lid 24. This ensures that the driving pin 64 does not simply slip over the lid 24 of the transducer housing 20 without opening it.

FIG. 7 shows the situation, where the tool's upper portion 14 has been fully turned around the axial direction 16. The lid 24 (the bayonet mount 26) is then open and the two guiding pins 56, 58 are completely arranged within the locking sections 60", 62" of the recesses 60, 62. In order to take out the opened transducer housing 20 the tool's upper portion 14 simply has to be turned back (in a clockwise manner) so that the upper portion 14 may be decoupled from the tool's base portion 12 and the transducer housing 20 can be manually unloaded.

In summary, a user simply has to enter the transducer housing 20 into the tool's base portion 12, then attach the tool's upper portion 14 thereto, and then turn the upper portion 14 relative to base portion 12. As soon as the bayonet mount 26 of the transducer housing 20 is open, the upper portion 14 may be turned back, decoupled from the base portion 12, and the opened transducer housing 20 may be manually unloaded.

Closing the bayonet mount 26 of the transducer housing 20 may be carried out in quite a similar way by using the same tool 10. The tool's upper portion 14 only has to be turned upside-down. In other words, the tool's upper portion 14 has to be flipped over. This situation is illustrated in FIGS. 8 and 9.

Figure 8:
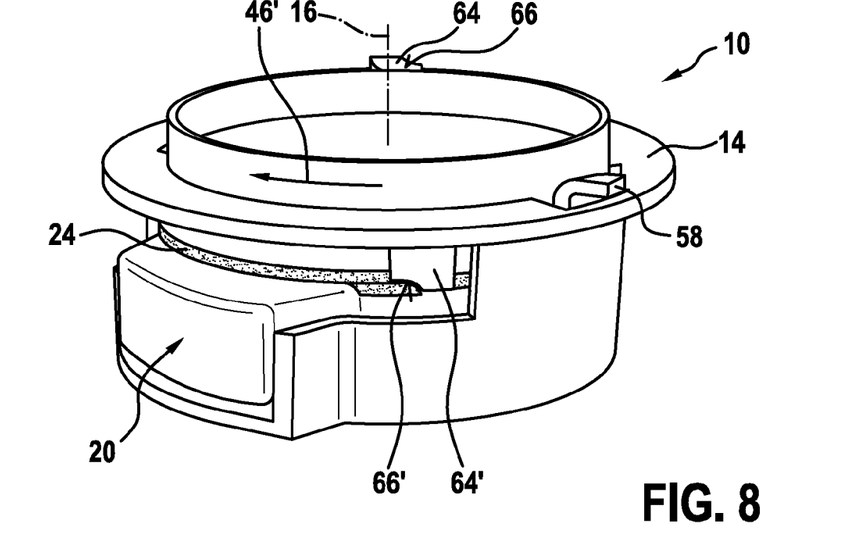
FIG. 8 shows a further perspective view of the tool according to the present invention in a fourth position.
Figure 9:
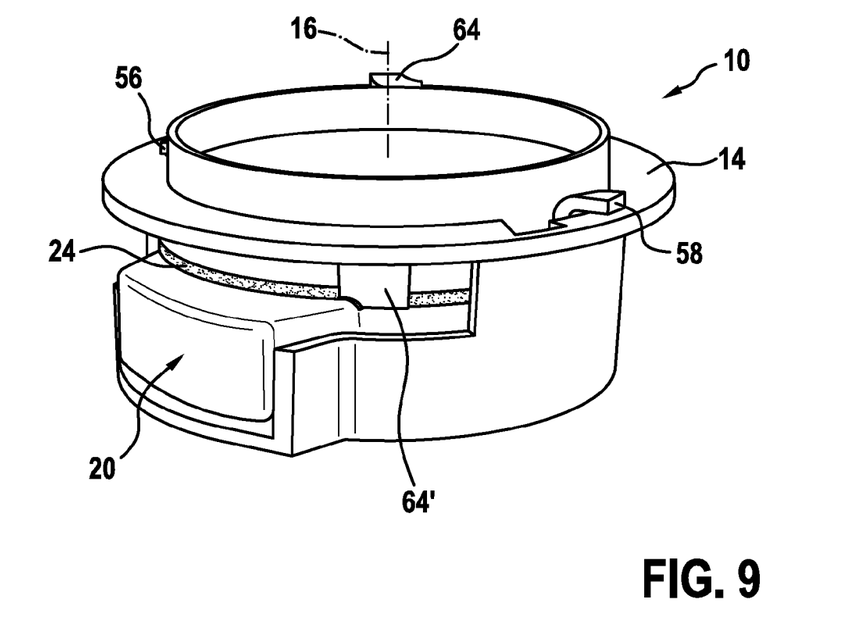
FIG. 9 shows an even further perspective view of the tool according to the present invention in a fifth position.

Compared to the situations shown in FIGS. 5 to 7, the tool's upper portion 14 is turned upside-down in FIGS. 8 and 9. A second driving pin 64' is then used to close the lid 24 of the transducer housing 20 upon a rotational movement of the tool's upper portion 14 in a clockwise manner (indicated by arrow 46'). This second driving pin 64' is arranged on an opposite side of the upper portion 14 and faces in a direction opposite to the first driving pin 64, which had been used for opening the lid 24. The second driving pin 64' comprises a second driving area 66' that faces in a direction opposite to the first driving area 66 of the first driving pin 64. Closing the lid 24 therefore works quite the same as opening it, except the difference that now the second driving pin 64' (and not the first driving pin 64) faces downwards, towards the transducer housing 20 and that the tool's upper portion 14 is rotated clockwise (instead of counter-clockwise).

Finally, it shall be stated that the tool 10 could of course also be constructed vice versa so that a clockwise movement of the tool's upper portion 14 would cause the lid 24 to open and a contrary counter-clockwise movement of the tool's upper portion 14 would cause the lid 24 to close.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A tool for opening and closing a transducer housing having two housing parts, a base body and a lid, that are coupleable with each other via a rotational coupling, wherein the tool comprises:
   a base portion forming a bowl for receiving the transducer housing and preventing a rotation of the base body of the transducer housing relative to the base portion of the tool around an axial direction of the tool; and
   an upper portion that is separate from the base portion and may be attached to the base portion, wherein a movement of the upper portion relative to the base portion in a radial direction, which is perpendicular to the axial direction, is mechanically prevented when the upper portion is attached to the base portion;
   wherein the base portion comprises a first engagement member and wherein the upper portion comprises a second engagement member which engages with the first engagement member when the upper portion is attached to the base portion,
   wherein the upper portion further comprises a driving pin having a driving area for contacting a corresponding contact area of the lid of the transducer housing for causing the lid of the transducer housing to move relative to the base body of the transducer housing in order to open or close the rotational coupling upon a rotational movement of the upper portion relative to the base portion around the axial direction; and
   wherein an engagement of the second engagement member with the first engagement member prevents a movement of the upper portion including the driving pin relative to the base portion along the axial direction during a contact between the driving area of the driving pin and the contact area of the lid of the transducer housing.

2. A tool according to claim 1, wherein the base portion comprises an inner wall and the upper portion comprises an outer wall that faces the inner wall of the base portion when the upper portion and the base portion are coupled with each other.

3. A tool according to claim 2, wherein at least a part of said inner wall of the base portion forms a form fit with at least a part of the outer wall of the upper portion, when the upper portion and the base portion coupled with each other, for preventing a movement of the upper portion relative to the base portion in the radial direction.

4. A tool according to claim 2, wherein a rotation of the base body of the transducer housing relative to the base portion of the tool around the axial direction is prevented through a form fit between the inner wall of the base portion of the tool and an outer surface of the transducer housing.

5. A tool according to claim 2, wherein the inner wall of the base portion has a cylindrically curved surface area, wherein parts of said inner wall deviate from the cylindrical shape and comprise a planar contact surface for contacting a corresponding contact surface of the transducer housing and preventing a rotation of the base body of the transducer housing relative to the base portion of the tool around the axial direction.

6. A tool according to claim 1, wherein the second engagement member is a recess in the upper portion, and wherein the first engagement member is a guiding pin which engages with said recess when the upper portion and the base portion are coupled with each other.

7. A tool according to claim 6, wherein the recess comprises an insertion section and an adjacent locking section, wherein the insertion section is larger than the locking section, wherein the guiding pin may be inserted into the insertion section, and wherein the guiding pin may be guided into the locking section upon a rotational movement of the upper portion relative to the base portion around the axial direction for clamping the guiding pin in axial direction.

8. A tool according to claim 1, wherein the base portion comprises a third engagement member and wherein the upper portion comprises a fourth engagement member which engages with the third engagement member when the upper portion and the base portion are coupled with each other.

9. A tool according to claim 1, wherein the driving area of the driving pin has a concave shape.

10. A tool according to claim 1, wherein the driving area of the driving pin is configured to establish a form fit with the contact area of the lid of the transducer housing upon contacting said contact area during the rotational movement of the upper portion relative to the base portion around the axial direction.

11. A tool according to claim 1, wherein the upper portion comprises two driving pins, a first driving pin with a first driving area for opening the rotational coupling of the transducer housing upon a rotational movement of the upper portion relative to the base portion around the axial direction, and a second driving pin with a second driving area for closing the rotational coupling of the transducer housing upon an oppositely oriented rotational movement of the upper portion relative to the base portion around the axial direction.

12. A tool according to claim 11, wherein the first driving pin and the second driving pin are arranged on opposite sides of the upper portion, and wherein the first driving area and the second driving area face in opposite directions.

13. A kit comprising:
a tool according to claim 1, and
a transducer housing having two housing parts, a base body and lid, that are coupleable with each other via a rotational coupling, wherein the lid comprises a contact area that is adapted to be contacted by a driving pin of the tool in order to open or close the transducer housing.

14. A transducer housing comprising:
a base body, and
a lid,
wherein the base body and the lid are coupleable with each other via a rotational coupling,
wherein the lid comprises a contact area that is adapted to be contacted by a driving pin of a tool in order to open or close the transducer housing upon a rotation of the lid relative to the base body around an axial direction, while a movement of the lid along the axial direction is prevented during said rotation, and
wherein the base body has a shape that is adapted to a base portion of said tool for preventing a rotation of the base body relative to the base portion of the tool around the axial direction.

15. A transducer housing according to claim 14, wherein the rotational coupling is a releasable bayonet mount.

* * * * *